(12) United States Patent
Banta et al.

(10) Patent No.: US 6,432,049 B1
(45) Date of Patent: Aug. 13, 2002

(54) ADJUSTABLE VAGINAL SPECULUM LIGHT

(76) Inventors: Linda Kay Banta, 1608 County Rd. 28; Gordon Lee Deter, 307 Manzanares La., both of Monte Vista, CO (US) 81144

( * ) Notice: Subject to any disclaimer, the term of this patent is extended or adjusted under 35 U.S.C. 154(b) by 0 days.

(21) Appl. No.: 09/651,664

(22) Filed: Aug. 29, 2000

(51) Int. Cl.[7] ................................................. A61B 1/07
(52) U.S. Cl. ........................ 600/249; 600/223; 600/245
(58) Field of Search ................................. 600/249, 245, 600/223, 221, 220, 199; 362/572, 581, 109, 183, 199, 197, 368, 370

(56) References Cited

U.S. PATENT DOCUMENTS

| | | | |
|---|---|---|---|
| 1,965,865 A | * | 7/1934 | Thompson |
| 2,320,709 A | * | 6/1943 | Arnesen |
| 3,592,199 A | * | 7/1971 | Ostensen |
| 3,789,835 A | | 2/1974 | Whitman |
| 3,881,468 A | * | 5/1975 | Foltz |
| 4,067,323 A | | 1/1978 | Troutner |
| 4,222,375 A | * | 9/1980 | Martinez |
| 4,597,383 A | | 7/1986 | VanDerBel |
| 4,619,248 A | * | 10/1986 | Walsh |

FOREIGN PATENT DOCUMENTS

DE 392904 A * 4/1924 .................. 600/223

* cited by examiner

Primary Examiner—Jeffrey A. Smith

(57) ABSTRACT

A small, lightweight, self contained light having a single cell rechargeable 3 volt battery and also having a support bracket with a device for attachment to the common metal speculum more often referred to as the Graves Metal Speculum. The light having a light tube being connected to the upper housing of the light body. This arrangement allows the light tube to swivel and tilt, permitting the light emitted from the end of the light tube to be precisely focused to the examination areas medial and lateral to the relative position of the opposing blades of the metal speculum.

20 Claims, 5 Drawing Sheets

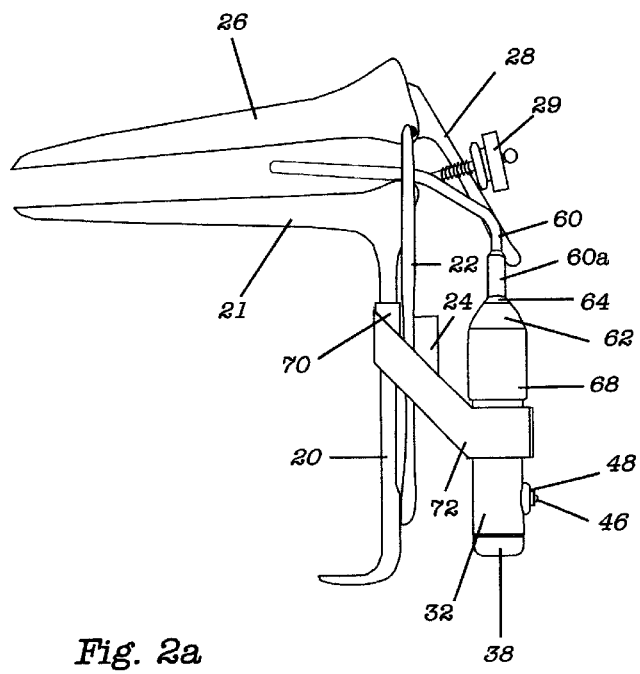
Fig 1
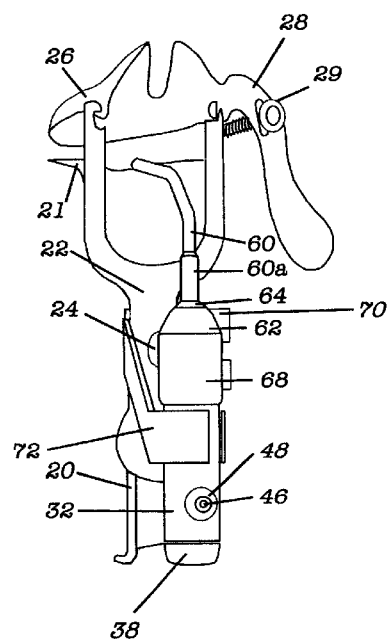
Fig. 2
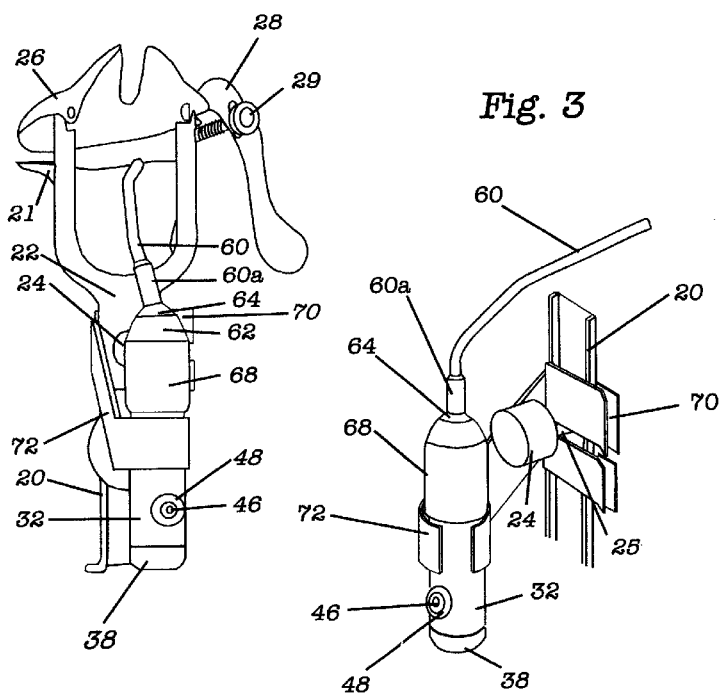
Fig. 2a
Fig. 3
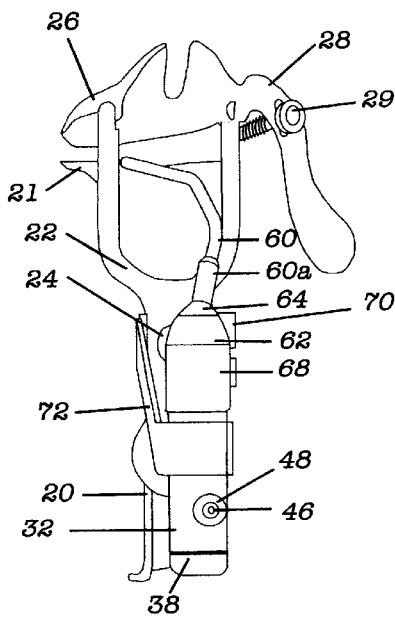
Fig. 2b

ADJUSTABLE VAGINAL SPECULUM LIGHT

BACKGROUND—FIELD OF INVENTION

This invention relates to medical devices, specifically a light that attaches to a metal speculum.

The metal speculum is a very useful instrument which allows the gynecologist or practicing family physician to examine the vaginal vault of female patients to discern the general health of the uterus and vaginal tissues. The metal speculum continues to be used on a regular basis with many physicians. A current problem lies with the physician's ability to illuminate the vaginal vault using the metal speculum. Many approaches have been used. Currently, the lack of useful lighting devices forces some physicians to use standard examination lights in a crude fashion when using the metal speculum.

Technical approaches to attach a light to the metal speculum have been few and have been limited in success. The problem is that there has never been an effective light that could be attached to the speculum and adjusted to pinpoint light to certain areas within the vaginal vault with the least amount of inconvenience to the physician.

BACKGROUND—DESCRIPTION OF PRIOR ART

Previous approaches to lighting the vaginal vault have been mostly unsuccessful. U.S. Pat. No. 3,789,835, Whitman was the most successful patent in terms of commercial viability. This device included an attachable light source to a modified grave's vaginal speculum. The problem with this design is that currently there are several manufacturers of the metal speculum ranging in sizes from small to large and not all metal speculums currently being used can accommodate this device, probably contributing to the current decline in usage of it. A second problem is the attachable fiber optic is subject to contamination of fluids, producing problems with sterility. Due to the positioning of the light source and cord attachment the instrument is likely to interfere with procedure. Lastly, the fiber optic only can be positioned shining light intermittent between the speculum blades to illuminate the deep interior of the vaginal cavity and cannot be adjusted. U.S. Pat No. 4,597,383, VanDerHal is an attachable tube light with fiber optic positioned intermediate between the speculum blades. The weakness of this design is that when the speculum is adjusted the light becomes loose causing loss of position to both. Therefore, frequent adjustments are made. Secondly this is a corded light which is subject to breakage under frequent use. Finally the position of the tube is fixed and non-adjustable.

OBJECTS AND ADVANTAGES

Accordingly, several objects and advantages of our invention are;

This device is cordless and rechargeable, providing convenience to the examiner and assistants.

This device provides an adjustable head whereby the examiner can focus the light beam in any direction and on any portion of the exposed vaginal tissues within the examination area unlike the fixed position light sources of prior aforementioned art.

The light tube being unobtrusive to examination instruments such as a biopsy gun, swabs, brushes and paddles as it is positioned in the lower blade area of the speculum.

By way of special attachment to the base of the speculum body, the light remains fixed to the speculum in a way that does not interfere with the adjustment of the speculum. Conversely, the adjustment of the speculum does not affect the position or alignment of the light device.

The position of the light is symmetrical staying within the axis and the bounds of the body of the speculum behind the main adjustment knob thereby not obstructing the flow of examination or procedure motion by protuberance.

This device is small and light weight. It will not weight the speculum down and pull on the speculum.

The light is made of durable materials that will provide years of service, without need of refitting of parts. The battery is designed for prolonged recharging cycles.

The light can be adjusted vertically within the holding band to adjust to varying sizes of the metal speculum.

The glass ball housing with the light tube can be removed from the main body and sterilized using heat sterilization methods.

Still, further objects and advantages will become apparent from consideration of the ensuing description and accompanying drawings.

SUMMARY

An adjustable vaginal speculum light comprising a light holding bracket with a device for attachment to the common metal speculum, a cylinder housing containing a rechargeable single cell power source, a lamp assembly attached to the cylinder housing, a light tube assembly threaded to the cylinder housing with an adjustable light tube to provide a adjustable beam of light to the lateral and medial areas between the blades of the metal speculum and a device for recharging the speculum light.

BRIEF DESCRIPTION OF THE DRAWINGS

FIG. 1 shows a side view of the metal vaginal speculum with adjustable light attached. The light tube is in a neutral position.

FIG. 2 shows a lower left oblique perspective view of the metal vaginal speculum with light attached. The light tube is in a neutral position.

FIG. 2a shows a lower left oblique perspective view of the metal vaginal speculum with light attached. The light tube is tilted and twisted to point to the right medial area between the upper and lower speculum blades.

FIG. 2b shows a left oblique perspective view of the metal vaginal speculum with light attached. The light tube is tilted and twisted to point to the left medial area between the upper and lower speculum blades.

FIG. 3 shows an upper right perspective of the light attached to section of base plate with threaded post and adjustment knob showing method of attachment with the metal clip.

REFERENCE NUMERALS

10 Molded Shell
12 Metal Recharge Contact Plate
14 Power Cord
20 Support Base Post
21 Lower Concave Shaped Blade
22 Riser
24 Tightening Knob
25 Threaded Bolt
26 Upper Blade
28 Control Bar
29 Adjustment Knob
30 Rubber Dust Ring
32 Cylinder Housing
32a Hole in Cylinder Housing
34 Metal Spring
36 Rubber Ring
38 End Cap
40 Upper Post
41 Positive Thermal Coefficient Resistor
41a Positive Lead Wire
41b Lamp Contact Wire
42 Recharge Wire
43 Lower Negative Contact Plate
44 Nylon Grommet
44a Grommet Cylinder
46 Steel Recharge Pin
48 Grommet Yoke
49 Rechargeable 3.0 Volt Lithium Metal Battery
50 Lamp Assembly Housing
50a Top Surface
50b Grounding Surface
51 Glass Bulb
52 Nylon Lamp Yoke
52a Formed Lip
53 Tungsten Filament
53a Positive Electrode Post
53b Negative Electrode Post
54 Lamp Bulb Jacket
54a Jacket Base
56 Metal Grounding Ring
58 Halogen Lamp Contact
58a Insulating Ring
60 Light Tube
60a Tube Tightening Cap
62 Glass Ball Housing Hat
62a Housing Hat Shoulder
64 Glass Ball Apron
64a Apron Threading
64b Apron Transition Shoulder
66 Tempered Clear Glass Ball
68 Glass Ball Housing
68a Housing Surface
68b Housing Cavity
68c Housing Barrel
68d Glass Ball Socket
70 Slotted Spring Steel Clip
72 Support Bracket
74 Holding Band
76 Insulating Sleeve

PREFERRED EMBODIMENT—DESCRIPTION

Figure 4:
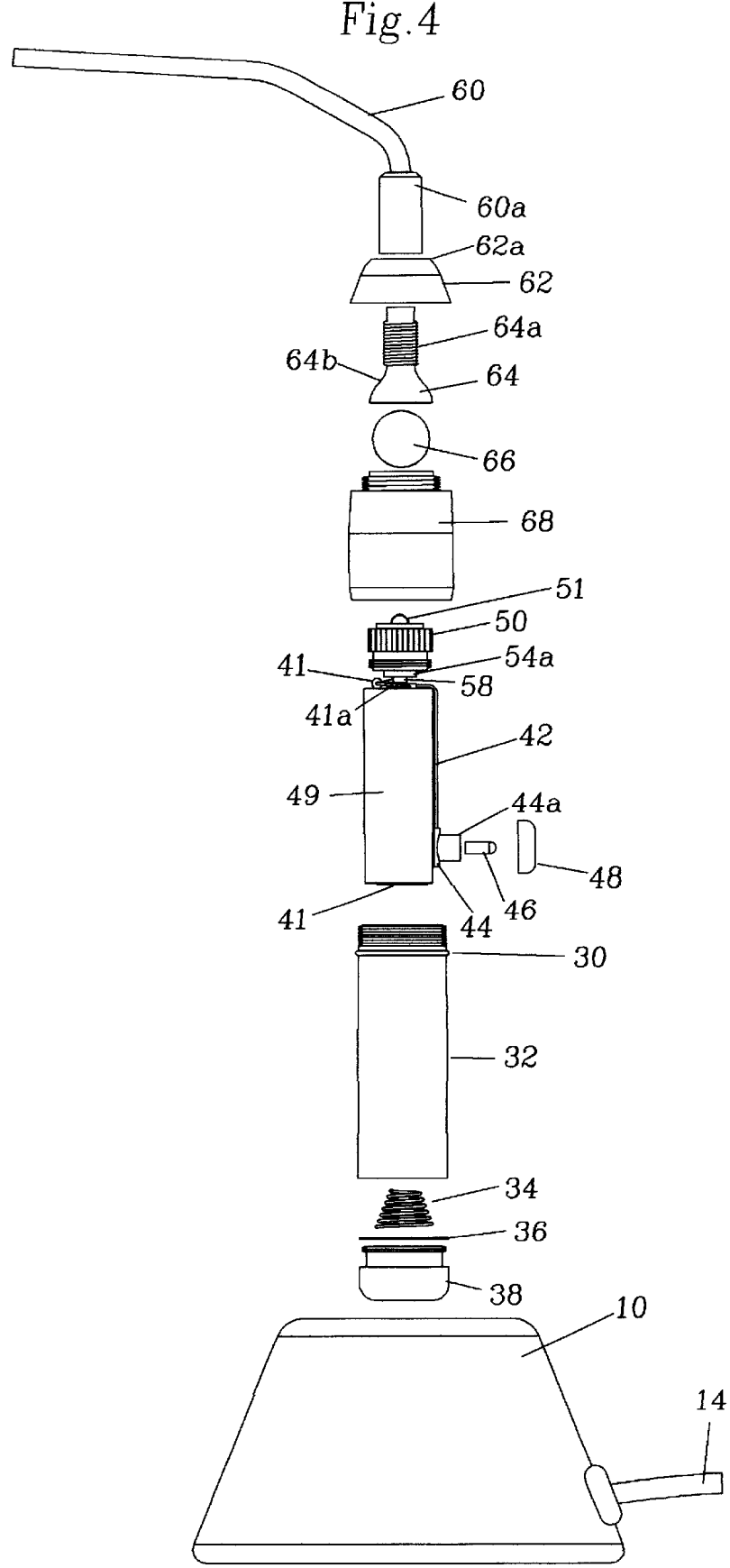
FIG. 4 shows an exploded side view of the adjustable vaginal speculum light.
Figure 5:
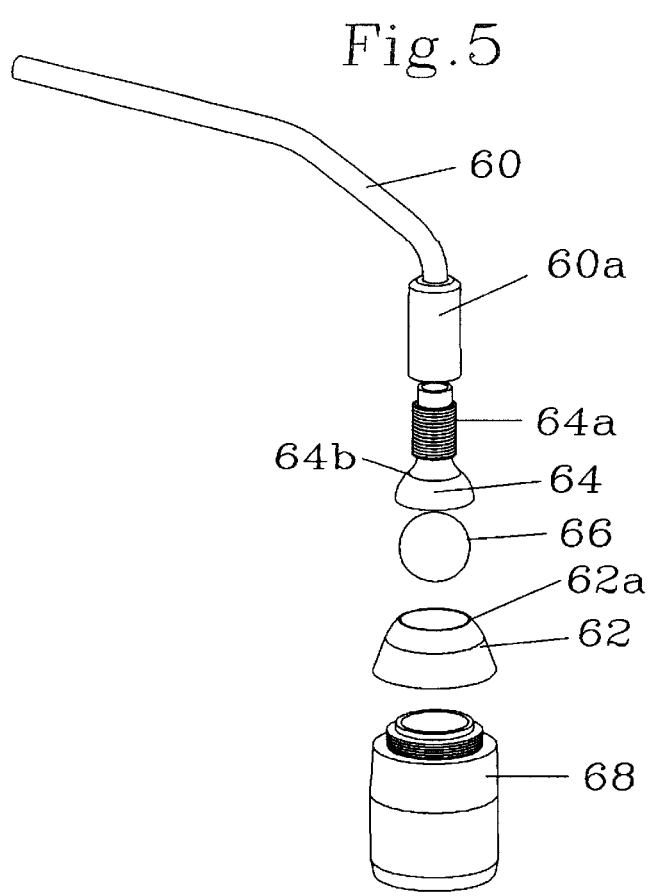
FIG. 5 shows an exploded perspective view of the upper head assembly with light tube.
Figure 6:
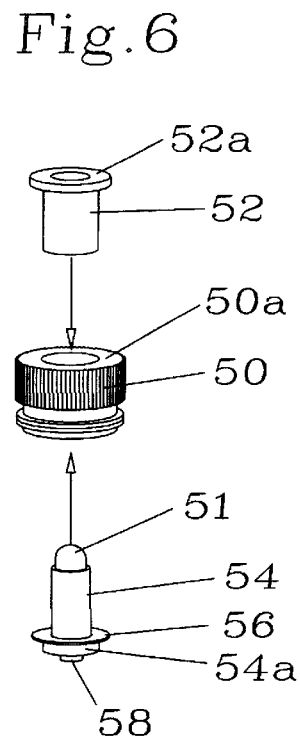
FIG. 6 shows an exploded perspective view of the medical light bulb assembly.
Figure 6A:
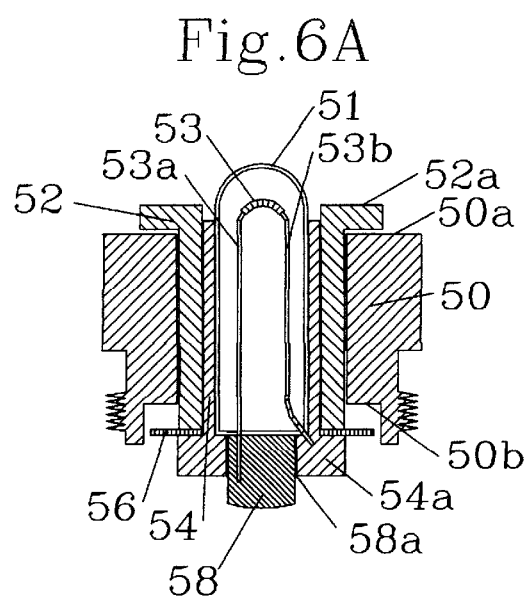
FIG. 6a shows a cross section of the medical light bulb assembly.
Figure 7:
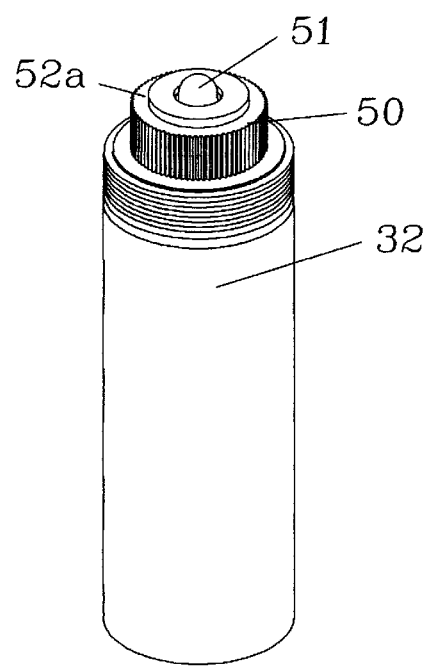
FIG. 7 shows a perspective view of the medical bulb assembly threaded into lower battery case.
Figure 8:
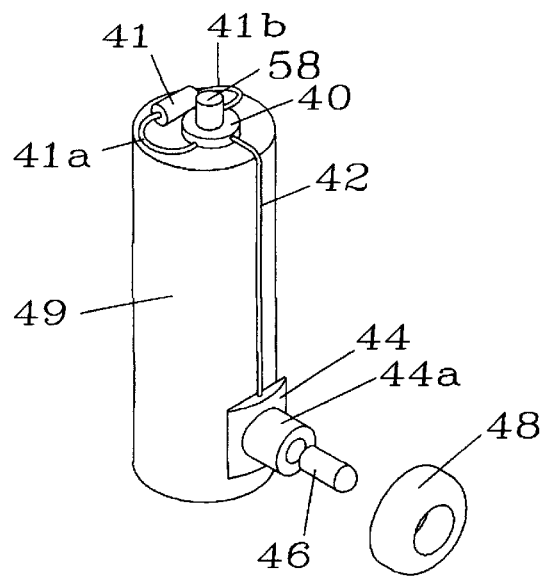
FIG. 8 shows an exploded perspective view of the battery and recharging component assembly.
Figure 9:
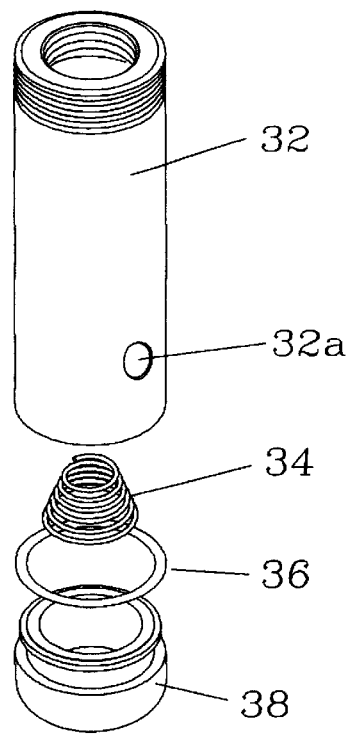
FIG. 9 shows an exploded perspective view of the lower battery case assembly.
Figure 10:
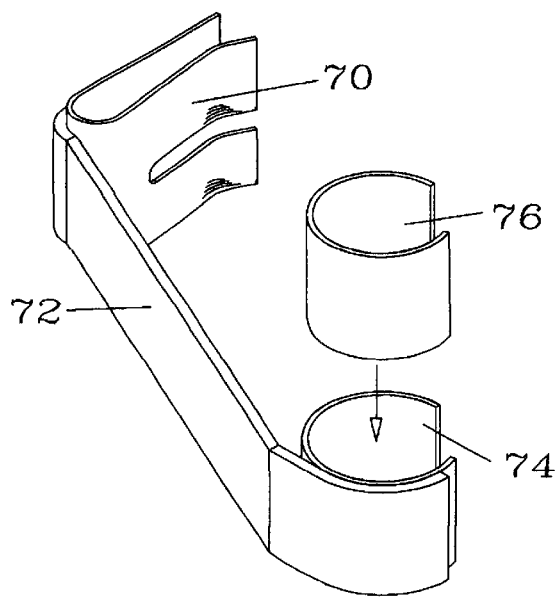
FIG. 10 shows an exploded view of the dip assembly, support bracket and retainer band.
Figure 11:
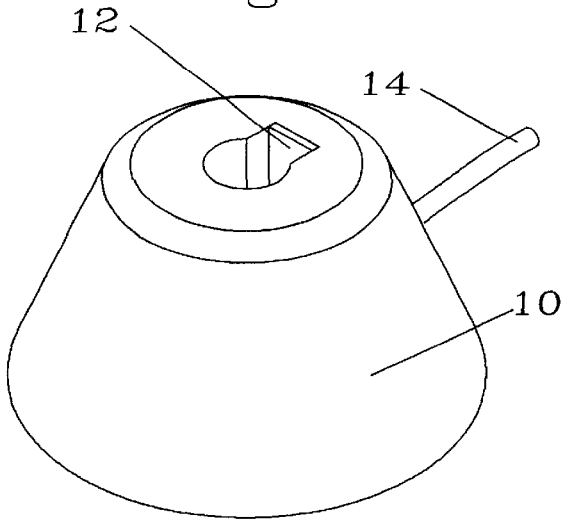
FIG. 11 shows a perspective view of the base charger unit.
Figure 12:
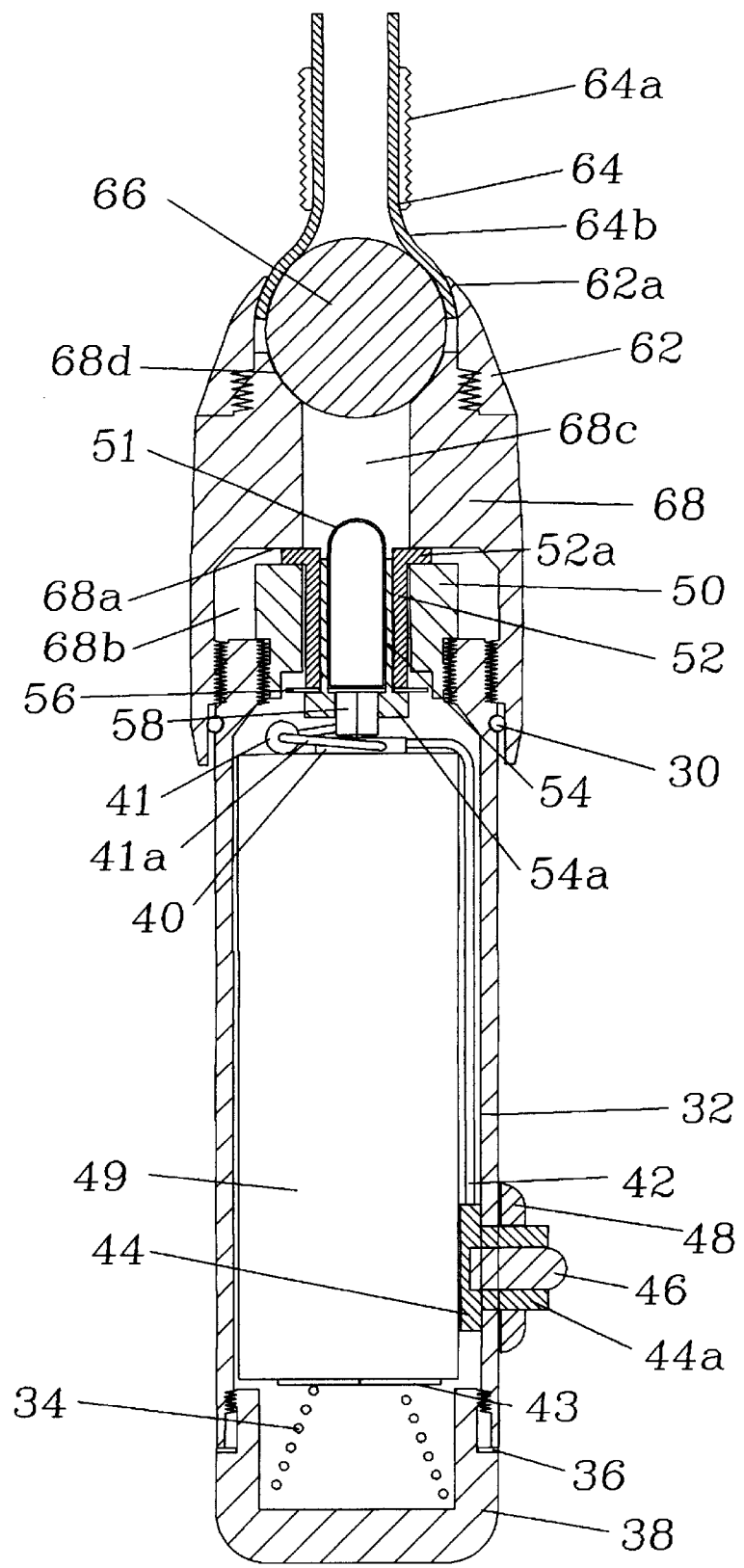
FIG. 12 shows a cross section of the adjustable light.

Referring to FIG. 1, FIG. 2, FIG. 2a, FIG. 2b and FIG. 3, we provide a metal speculum similar to the Graves Metal Speculum comprising a single supporting Base Post 20 rising vertically and bending laterally and widening to form the Lower Concave Shaped Blade 21 of the instrument. A rigid 'U' shaped Riser 22 formed to a single slotted vertical post attached to the Support Base Post 20 by means of a threaded bolt and a Tightening Knob 24 fixed to the Support Base Post 20. The Riser 22 can slide vertically along the Support Base Post 20 providing for an adjustable opening at the base of the cooperating speculum blades and be locked in position by the Tightening Knob 24. A Upper Blade 26 relatively shaped like the Lower Concave Shaped Blade 21, opposed in position and hinged on the two posts formed to the Riser 22, to work in cooperation and alignment with the Lower Concave Shaped Blade 21. A Control Bar 28 fixed to the Upper Blade 26 provides a functional lever for providing pressure in spreading the upper and lower blades apart in the vaginal vault. A Threaded Bolt 25 attached to the Support Base Post 20 and a Adjustment Knob 29 provides a means of locking the Control Bar 28 and the speculum blades in a open position. Referring to FIG. 10, a exploded view of the light holding assembly comprising a Slotted Spring Steel Clip 70, a Support Bracket 72, a Holding Band 74 and a Insulating Sleeve 76. The Slotted Spring Steel Clip 70 is positioned on the Support Base Post 20 and a Threaded Bolt 25 attached perpendicular and medial to the Support Base Post 20, between the front and back arm plates of the Slotted Spring Steel Clip 70 accommodating the Threaded Bolt 25 in the slot of the front arm plate of the Slotted Spring Steel Clip 70. The Support Bracket 72 forms to the back of the dip and slopes downward and away from the main body of the speculum, left of its center axis, forming to the Holding Band 74, with the Insulating Sleeve 76 inserted. The Holding Band 74 with the inserted Insulated Sleeve 76 holds the Cylinder Housing 32 of the adjustable light. Referring to FIG. 9, an exploded view of the lower battery case assembly consisting of a Cylinder Housing 32, a threaded End Cap 38 and a Metal Spring 34 nested within the hollow portion of the End Cap 38. The external threading of the End Cap 38 cooperates with the internal threading of the Cylinder Housing 32 casing. A Rubber Ring 36 provides a seal between abutting edges of the End Cap 38 and the Cylinder Housing 32. In combination, the End Cap 38 threaded to the Cylinder Housing 32 provides a hollow receptacle to encase a battery and a recharging component assembly as illustrated in FIG. 8 more preferably described as a Rechargeable 3.0 Volt Lithium Metal Battery 49 provided by Tadiran Electronic Industries with a Upper Post 40 and a Lower Negative Contact Plate 43. Upper Post 40 shall be made of a non conductive durable material. Shown in FIG. 8, a Positive Thermal Coefficient resistor 41 shall be electrically connected in series at the anterior end to the positive pole of the Rechargeable 3.0 Volt Lithium Metal Battery 49 beneath the Upper Post 40 by a Positive Lead Wire 41a. A Lamp Contact Wire 41b shall electrically connect the posterior end of the Positive Thermal Coefficient Resistor 41 to a Halogen Lamp Contact 58 as recommended by Tadiran Electronic Industries. A Recharge Wire 42 connects to the positive pole beneath Upper Post 40 to a Nylon Grommet 44. The Nylon Grommet 44 being fitted in the Hole In Cylinder Housing 32a and nesting a Steel Recharge Pin 46 which contacts the bared end of the Recharge Wire 42 within the Nylon Grommet 44. The Nylon Grommet 44 is held fixed to the side of Cylinder Housing 32 by friction between the Grommet Cylinder 44a and the Grommet Yoke 48. A small amount of play shall be afforded to tolerances between the Grommet Cylinder 44a and the Hole in Cylinder Housing 32a to allow for venting of pressurized air that will build within the Cylinder Housing 32 due to heat from the halogen lamp and changes in pressure within the housing due to mechanical motion of the adjustable head unit. The Cylinder Housing 32 receives a threaded halogen lamp assembly which is shown in an exploded perspective view in FIG. 6. Internal threading within the top end of the Cylinder Housing 32 is fashioned to cooperate with the external threading of a Lamp Assembly Housing 50 resulting in the Cylinder Housing 32 to be sealed by the Lamp Assembly Housing 50 thus enclosing the Rechargeable 3.0 Volt Lithium Metal Battery 49 and the recharging component assembly within the Cylinder Housing 32 as more fully shown in FIG. 7. As more fully shown in FIG. 6A, a Nylon Lamp Yoke 52 slips tightly over a Lamp Bulb Jacket 54 abutting to a Jacket Base 54a of the Lamp Bulb Jacket 54 thus securing a Metal Grounding Ring 56 between the abutting joint of the Nylon Lamp Yoke 52 and the Jacket Base 54a. A tight fit of the Nylon Lamp Yoke 52 around the Lamp Bulb Jacket 54 allows the halogen lamp within the Nylon Lamp Yoke 52 to be held within by friction. The Nylon Lamp Yoke 52 fitting to a tolerance to allow vertical travel of the halogen lamp within the barrel of the Lamp Assembly Housing 50. The Nylon Lamp Yoke 52 acts as a spacer between the Lamp Bulb Jacket 54 and the barrel wall of the Lamp Assembly Housing 50 to allow for guided vertical travel of the Nylon Lamp Yoke 52 and the affixed halogen lamp. This arrangement provides means for insulating the Lamp Bulb Jacket 54 from inadvertent grounding to the barrel wall of the Lamp Assembly Housing 50. The Nylon Lamp Yoke 52 provides a Formed Lip 52a. The lower surface of the lip is fashioned to rest on the Top Surface 50a of the Lamp Assembly Housing 50 to act as a stop of the halogen lamp in downward travel when light is in the off position. The upper surface of the Formed Lip 52a provides the contact point to the Housing Surface 68a of the Glass Ball Housing 68. In converse fashion, the Metal Grounding Ring 56 acts as a stop of vertical travel of the halogen lamp in upward travel, at the same time providing grounding of the Lamp Assembly Housing 50 to the Cylinder Housing 32 to engage the electrical circuit. A Glass Bulb 51 as shown in FIG. 6A formed within the Lamp Bulb Jacket 54 providing an enclosed capsule charged with halogen gas, fitted within a Tungsten Filament 53 with the Positive Electrode Post 53a extending through the Glass Bulb 51 to connect electrically to the Halogen Lamp Contact 58. The Halogen Lamp Contact 58 being insulated from the Lamp Bulb Jacket 54 by means of a Insulating Ring 58a. The contact being electrically connected to the Positive Thermal Coefficient resistor 41 by Lamp Contact Wire 41b. A Negative Electrode Post 53b being joined to the Jacket Base 54a, thereby completing the electrical circuit. A preferred embodiment of this arrangement would be to utilize a standard medical grade quartz halogen bulb with minor alterations to the design. An upper head assembly shown in an exploded view showing relative placement of parts is shown in FIG. 5. The Glass Ball Housing 68 is formed on the lower end to receive the upper Cylinder Housing 32. The external threading of the Glass Ball Housing 32 cooperates with the internal threading of the Glass Ball Housing 68. A Rubber Dust Ring 30 nested around the Cylinder Housing 32 provides a seal between the outside wall of the Cylinder Housing 32 and the internal barrel wall of the Glass Ball Housing 68. A Housing Cavity 68b formed within the main body of the Glass Ball Housing 68 provides sufficient room to accomodate the halogen lamp assembly. Shown in FIG. 12, the Housing Cavity 68b formed to a open Housing Barrel 68c leading to the Glass Ball Socket 68d. A Tempered Clear Glass Ball 66 is received with the Glass Ball Socket 68d and snugly seated to a tolerance to allow for free rotational motion of the Tempered Clear Glass Ball 66. A further embodiment shall be that the Glass Ball Socket 68d may be coated with a reflective PTFE coating. A Glass Ball Apron 64 is received by the Tempered Clear Glass Ball 66. The Glass Ball Apron 64 being formed to fit over the Tempered Clear Glass Ball 66 and extruded to a small canal to receive a Light Tube 60. The Glass Ball Apron 64 being fitted with Apron Threading 64a around the cylindrical portion of the Glass Ball Apron 64 to receive the Tube Tightening Cap 60a. A further embodiment shall be that the interior of the Glass Ball Apron 64 be coated with a light reflective PTFE coating. The Light Tube 60 being extruded as shown in FIG. 5 is received by the aforementioned Glass Ball Apron 64 and fixed to the apron by means of the Tube Tightening Cap 60a to work in cooperation with the Apron Threading 64a to secure a tight connection between the Light Tube 60 and the Glass Ball Apron 64. An embodiment of this arrangement shall be that the Light Tube 60 be filled with a clear plastic polymer having efficient light transmitting properties. A Glass Ball Housing Hat 62 is received by the Glass Ball Housing 68 allowing the narrow portion and the broadened shoulder area of the Glass Ball Apron 64 to pass through the center opening of the Glass Ball Housing Hat 62. The internal threading of the Glass Ball Housing Hat 62 is to be seated with the Glass Ball Housing 68. The resultant arrangement encapsulates the Tempered Clear Glass 66 and the broadened end of the Glass Ball Apron 64. The Housing Hat Shoulder 62a of the center opening of the Glass Ball Housing Hat 62 allows tolerance for movement of the Glass Ball Apron 64 around the Tempered Clear Glass Ball 66. Tolerance shall be engineered as to allow for free movement of the Glass Ball Apron 64 and the affixed Light Tube 60 but with sufficient friction to allow for fixed static positions of the Glass Ball Apron 64 with the attached Light Tube 60 when no external pressure is applied. A charger base shown in FIG. 11 consists of a Molded Shell 10, which preferably encases charging components know as the CH1S1P One Cell Battery Intelligent Charger as manufactured by Tadiran Electronic Industries being specifically engineered for the Tadiran-In-Charge Lithium Metal Battery as shown in FIG. 8. A Metal Recharge Contact Plate 12 electrically connects with the Steel Recharge Pin 46 by friction. A metal plate at the bottom of the base of the Molded Shell 10 provides the electrical ground to the Cylinder Housing 32 completing the charging circuit.

PREFERRED EMBODIMENT—OPERATION

Beginning with the light holding assembly shown in FIG. 10, the Support Bracket 72 will be attached by the Slotted Spring Steel Clip 70 and be attached to the Support Base Post 20 of the metal speculum as shown in FIG. 3. Tension between the blades of the Slotted Spring Steel Clip 70 and the rounded nature of the front blade urges the Slotted Spring Steel Clip 70 to pull laterally toward the central axis of the Support Base Post 20 and remaining fixed there by friction created by tension between the blades of the Slotted Spring Steel Clip 70. The Support Bracket 72 is formed and attached to the Slotted Spring Steel Clip 70 and extends downward and away from the speculum body to form and be affixed to the Holding Band 74. The Holding Band 74 preferably being made of spring steel, receives the Insulating Sleeve 76 which is affixed permanently thereto. The opening in the Holding Band 74 and the Insulating Sleeve 76 are aligned together. The resultant gap shall be large enough to allow for the Grommet Yoke 48 attached and adjacent to the Cylinder Housing 32 to pass through the formed opening. The Holding Band 74 and the affixed Insulating Sleeve 76 shall be fashioned to a tolerance slightly smaller than the diameter of the Cylinder Housing 32. The Holding Band 74 with attached Insulating Sleeve 76 shall expand when pressure is applied to accommodate the slightly larger Cylinder Housing 32 during the attachment of the fully assembled Adjustable Vaginal Speculum Light to the light holding assembly. The resultant tension between the Holding Band 74 and the Cylinder Housing 32 shall hold the light unit fixed. Sufficient tolerance shall be allowed by the Holding Band 74 to adequately hold the Adjustable Vaginal Speculum Light fixed but allow for slippage when upward or downward force is applied to the Adjustable Vaginal Speculum Light thus permitting vertical adjustment of the light to better fit varying sizes of the metal speculum.

Continuing to the preferred embodiment of the operation of the Adjustable Vaginal Speculum Light and beginning with the fully assembled static embodiment of the Speculum Light as described in the Main Embodiment, the Rechargeable 3.0 Volt Lithium Metal Battery 49 is urged upward due to the force produced by the Metal Spring 34 brought about by the Glass Ball Housing 68 being turned counterclockwise causing the Glass Ball Housing 68 to move upward on the upper external threading of the Cylinder Housing 32. Upward force is produced through the battery body and to the nonconductive Upper Post 40 so that it pushes upward against the Halogen Lamp Contact 58. This in turn causes the halogen lamp shown in FIG. 6a with the affixed Nylon Lamp Yoke 52 and the affixed Metal Grounding Ring 56 to move upward within the barrel of the Lamp Assembly Housing 50, stopping in vertical travel when the Metal Grounding Ring 56 connects with the inner Grounding Surface 50b of the Lamp Assembly Housing 50 causing an electrical ground to the housing of the Adjustable Vaginal Speculum Light allowing energy from the battery to flow from the Upper Post 40 through the Positive Lead Wire 41a, to the Positive Thermal Coefficient Resistor 41 and through the Lamp Contact Wire 41b to the Halogen Lamp Contact 58. The Positive Electrode Post 53a being affixed to the Halogen Lamp Contact 58 conducts current through and energizes the tungsten element. The electrical current returning through the Negative Electrode Post 53b to the Jacket Base 54a, being grounded to the Metal Grounding Ring 56. Conversely, when the Glass Ball Housing 68 is turned clockwise, a downward force is applied to the Formed Lip 52a of the Nylon Lamp Yoke 52 by the Housing Surface 68a causing the Nylon Lamp Yoke 52 downward through the Lamp Assembly Housing 50 and causing the affixed Metal Grounding Ring 56 to break contact with the housing thus stopping the flow of electrical current. It is my understanding by information provided to me by Tadiran Electronic Industries that as a result of the configuration described beforehand, the current is interrupted by the Positive Thermal Coefficient Resistor 41 if the battery load drops to 2 volts to protect damage to the battery.

Light is thus emitted by the halogen bulb within the Housing Barrel 68c and through the Tempered Clear Glass Ball 66 and directed by the Glass Ball Apron 64 into the affixed Light Tube 60. The clear plastic polymer within the Light Tube 60 transmits the light to the end of the Light Tube 60 and is projected beyond and into the examination area. The widened end of the Glass Ball Apron 64 is formed and encased between the Tempered Clear Glass Ball 66 and the Glass Ball Housing Hat 62 which swivels and twists upon the Tempered Clear Glass Ball 66. The tilting movement is limited to approximately 25 degrees from the vertical axis of the Adjustable Vaginal Speculum Light body as a result of the Apron Transition Shoulder 64b of the Glass Ball Apron 64 abutting against the Housing Hat Shoulder 62a.

A mean charging current of 80 mA is provided to the positive pole of the Rechargeable 3.0 Volt Lithium Metal Battery 49 via the Steel Recharge Pin 46 contacting the Metal Recharge Contact Plate 12 through the Recharge Wire 42. The ground circuit is completed through a metal grounding plate at the base of a Molded Shell 10 of the CH1S1P One Cell Battery Intelligent Charger contacting the bottom of the End Cap 38 through the Metal Spring 34 and to the Lower Negative Contact Plate 43 of the battery. It is my understanding by information provided to me by Tadiran Electronic Industries that the CH1S1P charger shall provide charging current to the Rechargeable 3.0 Volt Lithium Metal Battery 49 utilizing the charging configuration as described.

CONCLUSIONS, RAMIFICATIONS AND SCOPE

It can be seen that according to the invention, a small light weight rechargeable and adjustable light is produced that cooperates with the operation of and within the bounds of the Graves Metal Speculum.

Although the description above contains many specifics, these should not be construed as limiting the scope of the invention but as merely providing illustrations of some of the presently preferred embodiments of this invention. Various other embodiments and ramifications are possible with it's scope. For example, the Adjustable Vaginal Speculum Light may be constructed with any means of a light transmitting sphere in replacement of the tempered glass ball. A flexible medical grade light cable as seen on current endoscopes could be incorporated to the head assembly to produce a similar result of variable adjustability. Alternate methods of attachment of the Adjustable Vaginal Speculum Light to the Metal Speculum could be produced. The Adjustable Vaginal Speculum Light may be adapted for use with other forms and kinds of speculums and for possible attachment to and use for other medical instruments not here listed. Theoretically this light may be used as a general examination light in some circumstances. Positive impacts to the area of clinical medicine and remote field medicine can be anticipated by the introduction of this invention. Thus the scope of the invention should be determined by the appended claims and their legal equivalents, rather than by the examples given.

What is claimed:

1. An adjustable vaginal speculum light comprising:
   a. a light holding bracket, having a support bracket with means for attachment to a base of a metal vaginal speculum,
   b. a retainer band affixed to said support bracket having means for holding and supporting said adjustable vaginal speculum light within the bounds and axis of said metal vaginal speculum,
   c. a cylinder housing held by said retainer band containing a self contained rechargeable single cell power source having means for providing electrical power to said adjustable vaginal speculum light,
   d. said cylinder housing enclosing said rechargeable single cell power source within by a threaded halogen lamp assembly and whereby said threaded halogen lamp assembly having means for electrical connection to said rechargeable single cell power source, e. a cylindrical upper head assembly threaded to said cylinder housing enclosing said threaded halogen lamp assembly, directing light emanating from said threaded halogen lamp assembly through said cylindrical upper head assembly, f. said cylindrical upper head assembly further including a light tube contiguous to said cylindrical upper head assembly having means for transmitting light, g. said light tube in combination with a threaded cap having means for adjustment to provide for precise positioning of transmitted light between upper and lower blades of said metal vaginal speculum and to areas lateral of said upper and lower blades of said metal vaginal speculum, h. said adjustable vaginal speculum light having means for recharging said rechargeable single cell power source which is comprised of a molded plastic shell housing, said molded plastic shell housing recharging components within.

2. An adjustable vaginal speculum light as claimed in claim 1 wherein said means for attachment is a slotting spring steel clip.

3. An adjustable vaginal speculum light as claimed in claim 1 wherein said support bracket is configured to slope downward and away from a main body of said metal vaginal speculum forming to said means for holding and supporting said adjustable vaginal speculum light, which is a holding band, to hold said cylinder housing in a position parallel and centered to the axis of said metal vaginal speculum.

4. An adjustable vaginal speculum light as claimed in claim 1 further including an end cap secured by threads to said cylinder housing, said end cap nesting a metal spring to induce said rechargeable single cell power source in an upward direction.

5. An adjustable vaginal speculum light as claimed in claim 1 wherein said rechargeable single cell power source is a rechargeable 3.0 volt lithium metal battery.

6. An adjustable vaginal speculum light as claimed in claim 5 further including an positive lead wire connecting to a upper post of said rechargeable 3.0 volt lithium metal battery to a steel recharge pin which is held to the cylinder housing's side wall by a nylon grommet and a grommet yoke.

7. An adjustable vaginal speculum light as claimed in claim 6 wherein said positive pole of said rechargeable 3.0 volt lithium metal battery is connected electrically by said positive lead wire to a anterior end of a positive thermal coefficient resistor.

8. An adjustable vaginal speculum light as claimed in claim 7 wherein the posterior end of said positive thermal coefficient resistor is connected electrically by a lamp contact wire to a halogen lamp contact.

9. An adjustable vaginal speculum light as claimed in claim 8 wherein said halogen lamp contact is incorporated in said threaded halogen lamp assembly.

10. An adjustable vaginal speculum light as claimed in claim 9 wherein said threaded halogen lamp assembly also is comprised of a metal grounding ring which encircles a base of a lamp bulb jacket, said lamp bulb jacket being made of a metal material, further including a nylon lamp yoke which holds said lamp bulb jacket within a lamp assembly housing.

11. An adjustable vaginal speculum light as claimed in claim 10 wherein said upper post urges a glass bulb encased in said lamp bulb jacket and said nylon lamp yoke upward through said lamp assembly housing when said rechargeable 3.0 volt lithium metal battery is urged in an upward direction, inducing said metal grounding ring to ground to said lamp assembly housing and in turn to a body of said adjustable vaginal speculum light thereby inducing an electrical current to flow through said positive thermal coefficient resistor to said halogen lamp contact and through a positive electrode post, a tungsten filament and a negative electrode post connected thereto.

12. An adjustable vaginal speculum light as claimed in claim 5 further including a lower negative contact plate affixed to the base of said rechargeable 3.0 volt lithium metal battery and an upper post made of nonconductive material being contiguous with and affixed to a positive pole of said rechargeable 3.0 volt lithium metal battery.

13. An adjustable vaginal speculum light as claimed in claim 1 having said means for adjustment of said light tube which further includes a glass ball housing and a glass ball housing hat, said glass ball housing hat is contiguous with and threaded cooperatively to said glass ball housing.

14. An adjustable vaginal speculum light as claimed in claim 1 having said means for adjustment of said light tube which further includes a tempered clear glass ball and a glass ball apron.

15. An adjustable vaginal speculum light as claimed in claim 14 wherein said glass ball apron is saddled over the top of said tempered clear glass ball allowing for multidirectional movement of said glass ball apron over said tempered clear glass ball.

16. An adjustable vaginal speculum light as claimed in claim 15 wherein said tempered clear glass ball in combination with said glass ball apron is nested in a glass ball housing in a way that an apron transition shoulder is sandwiched between said tempered clear glass ball and an interior portion of a glass ball housing hat, said apron transition shoulder and said tempered clear glass ball also being encased between said glass ball housing and said glass ball housing hat.

17. An adjustable vaginal speculum light as claimed in claim 1 wherein said light tube is inserted into and affixed to a tube tightening cap.

18. An adjustable vaginal speculum light as claimed in claim 1 wherein said light tube has, two bends to position the light emitting end of said light tube at an angle approximately parallel to a main axis of upper and lower blades of said metal vaginal speculum when said light tube is in a centered position.

19. An adjustable vaginal speculum light as claimed in claim 1 wherein said light tube is filled with a clear plastic light transmitting polymer.

20. An adjustable vaginal speculum light as claimed in claim 1 wherein said adjustable vaginal speculum light is comprised of at least one metal material.

* * * * *